(12) United States Patent
Banerjee et al.

(10) Patent No.: US 8,401,199 B1
(45) Date of Patent: Mar. 19, 2013

(54) AUTOMATIC PERFORMANCE OPTIMIZATION FOR PERCEPTUAL DEVICES

(75) Inventors: Bonny Banerjee, Palm Bay, FL (US); Lee Krause, Indialantic, FL (US)

(73) Assignee: Cochlear Limited, Macquarie University, NSW (AU)

( * ) Notice: Subject to any disclaimer, the term of this patent is extended or adjusted under 35 U.S.C. 154(b) by 976 days.

(21) Appl. No.: 12/185,398

(22) Filed: Aug. 4, 2008

(51) Int. Cl.
  *H04R 29/00* (2006.01)
  *H04R 25/00* (2006.01)
(52) U.S. Cl. ............. 381/58; 381/60; 381/314; 600/559
(58) Field of Classification Search ................ 381/58, 381/60, 312, 314; 600/559; 607/56, 57
  See application file for complete search history.

(56) References Cited

U.S. PATENT DOCUMENTS

| | | | |
|---|---|---|---|
| 4,049,930 A | | 9/1977 | Fletcher et al. |
| 4,327,252 A | | 4/1982 | Tomatis |
| 4,953,112 A | * | 8/1990 | Widin et al. ................ 703/6 |
| 5,008,942 A | | 4/1991 | Kikuchi |
| 5,729,658 A | | 3/1998 | Hou et al. |
| 6,004,015 A | * | 12/1999 | Watanabe et al. ............... 700/28 |
| 6,035,046 A | | 3/2000 | Cheng et al. |
| 6,036,496 A | | 3/2000 | Miller et al. |
| 6,118,877 A | | 9/2000 | Lindermann et al. |
| 6,446,038 B1 | | 9/2002 | Bayya et al. |
| 6,684,063 B2 | | 1/2004 | Berger et al. |
| 6,763,329 B2 | | 7/2004 | Brandel et al. |
| 6,823,171 B1 | | 11/2004 | Kaario |
| 6,823,312 B2 | | 11/2004 | Mittal et al. |
| 6,913,578 B2 | * | 7/2005 | Hou .............................. 600/559 |
| 6,914,996 B2 | | 7/2005 | Takeda |

(Continued)

FOREIGN PATENT DOCUMENTS

| | | |
|---|---|---|
| DE | 2349626 | 4/1975 |
| EP | 0714069 | 5/1996 |

(Continued)

OTHER PUBLICATIONS

Rabiner, et al. "A Tutorial on Hidden Markov Models and Selected Applications in Speech Recognition," vol. 77, No. 2, Feb. 1989, pp. 257-269.

(Continued)

*Primary Examiner* — Calvin Lee
*Assistant Examiner* — Scott Stowe
(74) *Attorney, Agent, or Firm* — Merchant & Gould PC (57) ABSTRACT

Systems and methods may be used to modify a controllable stimulus generated by a digital audio device in communication with a human user. An input signal is provided to the digital audio device. In turn, the digital audio device sends a stimulus based on that input signal to the human user, who takes an action, usually in the form of an output signal, to characterize the stimulus that the user receives, based on the user's perception. An algorithm then determines a difference between the input signal and the output signal, and a perceptual model is constructed based at least in part on the difference. Thereafter, a new value for the parameter of the digital audio device is suggested based at least in part on the perceptual model. This process continues iteratively until the algorithm finds the user's optimal device parameters. While this process is highly complex and time consuming, the algorithm successfully reaches at least a near optimal settings, if not the optimal, in a short time.

10 Claims, 8 Drawing Sheets

U.S. PATENT DOCUMENTS

| | | |
|---|---|---|
| 7,206,416 B2 | 4/2007 | Krause et al. |
| 2002/0120440 A1 | 8/2002 | Zhang |
| 2003/0007647 A1 | 1/2003 | Nielsen et al. |
| 2005/0027537 A1 | 2/2005 | Krause et al. |
| 2006/0045281 A1 | 3/2006 | Korneluk et al. |
| 2007/0286350 A1 | 12/2007 | Krause et al. |
| 2010/0027800 A1 | 2/2010 | Banerjee et al. |
| 2010/0299148 A1 | 11/2010 | Krause et al. |

FOREIGN PATENT DOCUMENTS

| | | |
|---|---|---|
| EP | 1519625 | 3/2005 |
| JP | 2002-291062 | 10/2002 |
| WO | WO 98/44762 | 10/1998 |
| WO | WO-99/31937 | 6/1999 |
| WO | WO 2005/062776 | 7/2005 |

OTHER PUBLICATIONS

Skowronski, et al., "Exploiting independent filter bandwidth of human factor cepstral coefficients in automatic speech recognition," J. Acoustical Society of America, vol. 116, No. 3, pp. 1774-1780, Sep. 2004.

Skowronski, M. D. et al., "Applied principles of clear and Lombard speech for intelligibility enhancement in noisy environments," Speech Communication, vol. 48, No. 5, pp. 549-558, May 2006.

\* cited by examiner

AUTOMATIC PERFORMANCE OPTIMIZATION FOR PERCEPTUAL DEVICES

FIELD OF THE INVENTION

This invention relates to systems and methods for optimizing performance of perceptual devices to adjust to a user's needs and, more particularly, to systems and methods for adjusting the parameters of digital hearing devices to customize the output from the hearing device to a user.

BACKGROUND OF THE INVENTION

Perception is integral to intelligence. Perceptual ability is a prerequisite for any intelligent agent, living or artificial, to function satisfactorily in the real world. For an agent to experience an external environment with its perceptual organs (or sensors, in the case of artificial agents), it sometimes becomes necessary to augment the perceptual organs, the environment, or both.

For example, human eyes are often augmented with a pair of prescription glasses. In another example, to experience surround-sound in a car or in a home theater, the environment is augmented with devices, such as speakers and sub-woofers, placed in certain positions with respect to the agent. To experience a 3D movie, the agent often has to wear specially designed eyeglasses, such as polarized glasses. These and other devices including, without limitation, audio headphones, hearing aids, cochlear implants, low-light or "night-vision" goggles, tactile feedback devices, etc., may be referred to generally as "perceptual devices."

Due to personal preference, taste, and the raw perceptual ability of the organs, the quality of experience achieved by augmenting the agent's perceptual organs or environment with devices is often user-specific. As a result, the devices should be tuned to provide the optimum experience to each user.

With the advent of sophisticated perceptual devices, each having a large number of degrees of freedom, it has become difficult to tune such devices to the satisfaction of each user. Many devices are left to the user for ad-hoc self-tuning, while many others are never tuned because the time and cost required to tune a device for a user may be too high. For example, cochlear implant devices, often used by people having severe hearing-impairment, are virtually never tuned by an audiologist to a particular user, but instead are left with the factory default settings to which the user's brain must attempt to adjust. Thus, a hearing-impaired person may never get the full benefit of his cochlear implant.

Agents with simple perceptual systems (e.g., robotic vacuum cleaners) have sufficient transparency to allow for the tracking of their raw perceptual abilities, while agents with complex perceptual systems (e.g., humans) lack that transparency. Hence, it is extremely difficult to tune devices to the satisfaction of members of the latter class of users, because of the complexity of the devices that enhance an already complex perceptual system.

A sophisticated perceptual device should also allow the user to tune the device to meet that user's particular perceptual needs. Such complex devices often have a large set of parameters that can be tuned to a specific user's needs. Each parameter can be assigned one of many values, and determining the values of parameters for a particular user's optimum performance is difficult. A user is required to be thoroughly tested with the device in order to be assigned the optimum parameter values. The number of tests required increases exponentially with the number of device parameters. Dedicating a significant amount of time to testing often is not a feasible option; accordingly, it is may be advantageous to reduce the complexity of the problem.

Therefore, there is a need to automatically tune perceptual devices in a user-specific way. As of today, living agents, especially humans, have complex perceptual systems that can take advantage of a user-specific tuning method. Artificial agents with complex perceptual systems, when developed, will also benefit from the user-specific tuning method.

SUMMARY OF THE INVENTION

In one aspect, embodiments of the invention provide a method for modifying a controllable stimulus generated by a digital audio device in communication with a human user, the method including: generating an input signal to the digital audio device, the digital audio device sending a stimulus to the human user, the stimulus defined at least in part by a parameter, the parameter comprising a value; receiving an output signal from the user, the output signal based at least in part on a perception of the stimulus by the human user; determining a difference between the input signal and the output signal; constructing a perceptual model based at least in part on the difference; and suggesting a value for the parameter of the digital audio device based at least in part on the perceptual model.

In one embodiment, suggesting a value further includes utilizing a knowledge base. In another embodiment, the knowledge base includes at least one of declarative knowledge and procedural knowledge. In another embodiment, the method includes generating a second input signal to the digital audio device based at least in part on the perceptual model.

In another aspect, embodiments of the present invention provide a system for modifying a controllable stimulus generated by a digital audio device in communication with a human user, the system including: a test set generator for generating a test set for the digital audio device, the digital audio device sending a stimulus to the human user, the stimulus defined at least in part by a parameter, the parameter having a value; a signal receiver for receiving an output signal from the human user, the output signal based at least in part on a perception of the stimulus by the human user; a perceptual model module receiving and storing information concerning the output signal from the signal receiver; and a parameter value generator for applying at least one algorithm to the information and modifying a parameter value based at least in part on the application of the algorithm to the information, wherein the at least one algorithm includes at least one of a uniform sampling algorithm, a neighborhood sampling algorithm, an average sampling algorithm, and a predefined criteria algorithm. In one embodiment, the perceptual model is a surface model.

In another embodiment, the at least one algorithm is a uniform sampling algorithm, and the parameter value generator includes: a point identification module for identifying a plurality of sampled points; an area identification module for identifying a plurality of projected areas, wherein each projected area is characterized by an absence of any of the plurality of sampled points; a projected point identification module for identifying a projected point associated with a first projected area so as to reduce the size of an unsampled area for subsequent iterations. In another embodiment, the first projected area includes an area greater than an area of each of the plurality of projected areas. In still another embodiment, the projected areas are circles. In yet another embodiment, the projected points are the centers of the circles.

In another embodiment, the algorithm includes a neighborhood sampling algorithm and the parameter value generator includes: a first point identification module for identifying a first sampled point; a second point identification module for identifying a second sampled point on a first line from the second sampled point to the first sampled point; and an projected point identification module for identifying at least one of (i) a projected point on the first line proximate the first sampled point and (ii) a null point condition. In some embodiments, the first point identification module identifies the first sampled point from a plurality of sampled points. In certain embodiments, the first point identification identifies by first sampled point by assigning a confidence to at least one of the plurality of sampled points.

In still another embodiment, the first line has a slope describing a downward direction. In yet another embodiment, the first line has a maximum downward slope. In another embodiment, the maximum downward slope is relative to a third sample point located on a second line from the third sample point to the first sample point.

In another embodiment, the algorithm includes an average sampling algorithm and the parameter value generator includes: a mean error calculator for computing a mean error of each of a sampled value of a plurality of parameters; a sorter for sorting the sampled value of each of the plurality of parameters based at least in part on the mean error; a point selector for selecting at least one of (i) a projected point including a first predetermined mean error of a parameter and (ii) a projected point including a second predetermined mean error. In another embodiment, the sorter sorts the sampled values in ascending order. In another embodiment, the first predetermined mean error is a minimum error. In still another embodiment, the second predetermined error is a next best point. In still another embodiment, the algorithm includes a predefined criteria algorithm. In yet another embodiment, the predefined criteria algorithm includes a characterizing algorithm that characterizes the user based on a predefined criterion.

BRIEF DESCRIPTION OF THE DRAWINGS

Other features and advantages of the present invention, as well as the invention itself, can be more fully understood from the following description of the various embodiments, when read together with the accompanying drawings, in which.

DETAILED DESCRIPTION OF THE INVENTION

Various embodiments of the methods and systems disclosed herein are used to "tune" a perceptual device. In this application, the term "optimization" is sometimes used to describe the process of tuning, which typically includes modifying parameters of a perceptual device. However, one of ordinary skill in the art would understand that the disclosed methods and systems may be used to "modify" the parameters of a device without achieving "optimization." That is, there may be instances where limitations of a device, or of user perception, may prevent complete optimization of a parameter, where "optimization" could be characterized as obtaining perfect or near-perfect results.

Another consideration is that the testing associated with the tuning process may stop short when the tester becomes tired or otherwise stops the test, without completely "optimizing" the device. True "optimization" may not be necessary or desirable, as even seemingly minor improvements or modifications to a device parameter may produce significant positive results for a device user. Accordingly, the terms "optimization," "modification," "tuning," "adjusting," and like terms are used herein interchangeably and without restriction to describe systems and methods that are used to modify parameters of a perceptual device, notwithstanding whether the output from the device is ultimately "optimized" or "perfected," as those terms are typically understood.

Embodiments of the disclosed methods and systems automatically tune at least one device parameter based on a user's raw perceptual ability to improve the user's perception utilizing different tuning algorithms operating separately or in tandem to allow the device to be tuned quickly. The device parameters can be user-specific or user-independent. In one embodiment of the optimization method, a model is created to describe a user's perception (i.e., the perceptual model). This model is incremental and is specific to a user and his device. Next, one or more algorithms is applied to the model resulting in predictions (along with confidence and explanation) of the optimum parameter values for the user. Then, the user is iteratively tested with the values having the highest confidence, and the model is further updated. Last, a set of rules capturing user-independent information is used to tune certain parameters.

The number of parameters governing the operation of a given perceptual device may be large. The amount of data required to faithfully model a user's perceptual strengths and weaknesses using that device increases exponentially with the number of device parameters; this limits the ability to reach optimal settings for the device in a reasonable time. In one embodiment, a number of algorithms are used with simple independent assumptions regarding the model. Using these assumptions, each algorithm studies the model and makes predictions with a confidence. The most confident prediction is chosen at any point of time. This architecture helps reduce the complexity of the solution that otherwise would have been enormous.

In this context, a user may be considered a black box with perceptual organs that can accept a signal as input and produce a signal as output in accordance with certain instructions. This method is useful for applications where the black box is too complex to be modeled non-stochastically, such as the human brain. Depending on the nature of the "black box," the instructions can be conveyed by different means. For example, a human might be told instructions in a natural language; an artificial agent might be programmed with the instructions.

Raw perception of a user is judged by some criteria that measure the actual output signal against the output signal expected from the application of the given set of instructions to the input signal. For example, if the input signals are spoken phonemes, the black box is a human brain with ears as the perceptual organs, and the instruction is to reproduce the input phonemes (as speech or in writing), the perception might be measured by computing the difference between the input and output phonemes. In another example, if the input signal is a set of letters written on a piece of paper, the black box is a human brain with eyes as the perceptual organs, and the instruction is to reproduce the letters (as speech or in writing), the perception might be measured by computing the difference between the input and output letters. It is assumed that the instructions have been correctly conveyed and are being followed by the black box.

Figure 1:
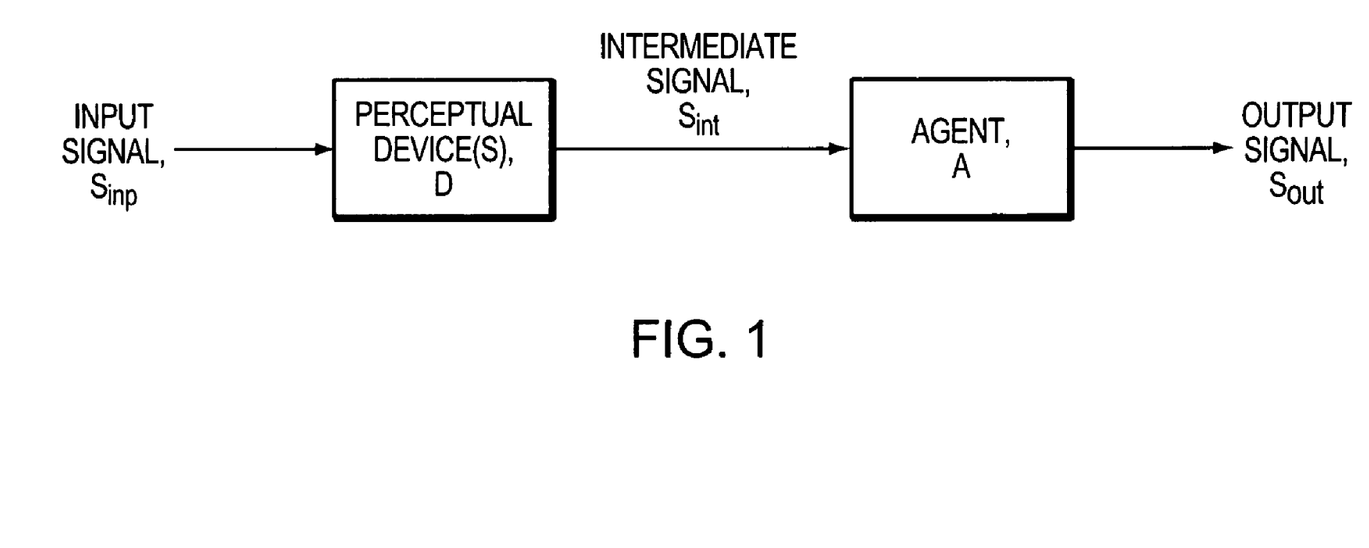
FIG. 1 is a schematic diagram depicting the relationship between a perceptual device and an agent in accordance with one embodiment of the present invention.

FIG. 1 depicts an exemplary relationship between the perceptual device D and the agent A. Given a user or an agent A, one or more devices D, an input signal $S_{inp}$ and a corresponding output signal $S_{out}$ that the agent has produced obeying certain instructions, FIG. 1 depicts the relationships:

$$D(S_{inp}) = S_{int}$$

$$A(S_{int}) = S_{out}$$

$$\therefore A(D(S_{inp})) S_{out}$$

where $S_{int}$ is the intermediate signal or stimulus emanated from the device(s) and perceived by the agent. In the case of a digital audio device, the stimulus is the sound actually heard by the user. The intermediate signal cannot be measured in the same way that $S_{inp}$ and $S_{out}$ are susceptible of measurement. It is desired that $S_{inp} = S_{out}$, hence $A(D(.)) = I(.)$ where $I(.)$ is the identity function.

In a typical application of the current invention, almost nothing is known about the function A. The function D is characterized by the device parameters. Embodiments of the present invention (1) statistically model the perceptual errors (i.e., some metric applied to $S_{inp} \sim S_{out}$) for an agent with respect to the device parameters, and (2) study this perceptual model to predict the best set of parameter values. Ideally, the predicted parameter values render $S_{inp} = S_{out}$ for any $S_{inp}$ for the agent and the device. Thus, in general, the present invention proposes a general method for estimating the function $A(D(.))$ where minimal knowledge is available regarding function A.

Figure 2:
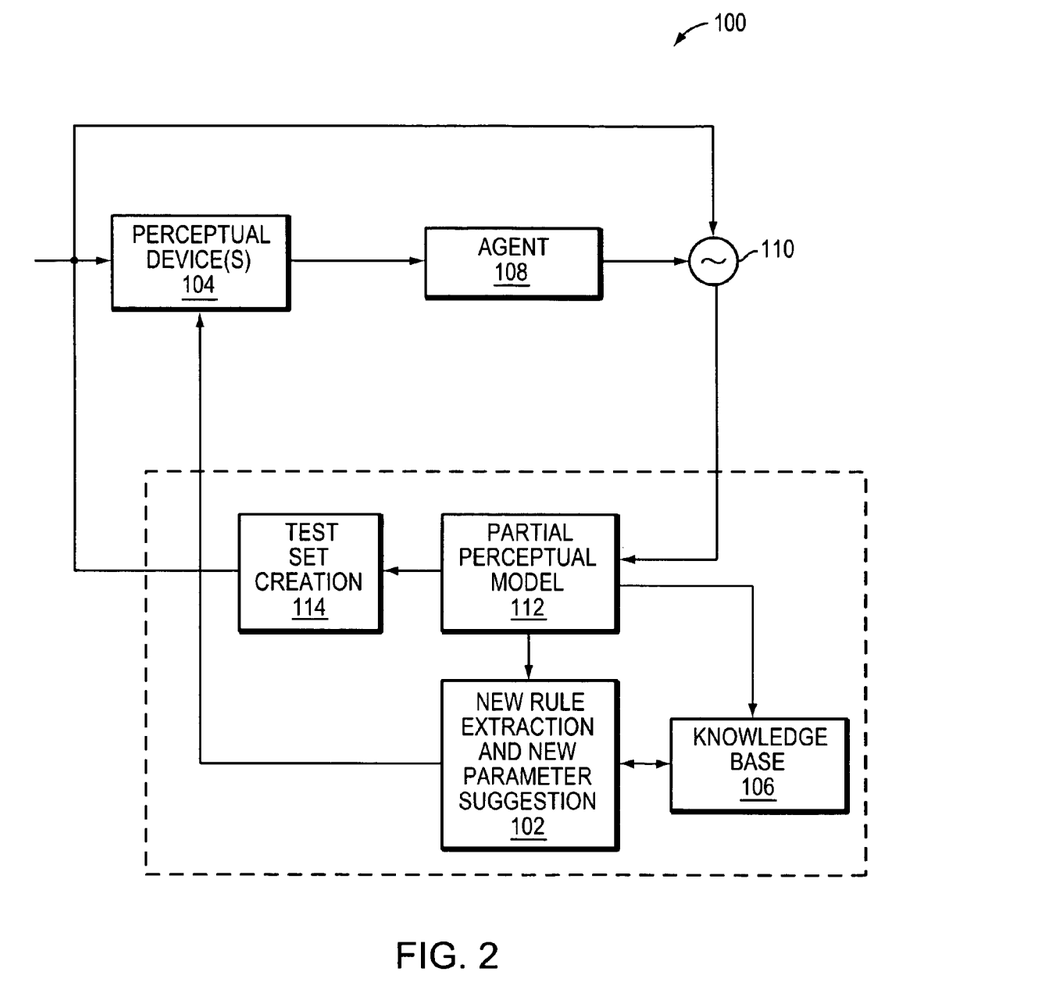
FIG. 2 is a schematic diagram of an apparatus in accordance with one embodiment of the present invention.

In one embodiment of the present invention, a method is provided for automatically tuning the parameters of at least one perceptual device in a user-specific way. The agent or its environment is fitted with a device(s) whose parameters are preset, for example, to factory default values. The proposed method may be implemented as a computer program that tests the raw perception of the agent. FIG. 2 depicts one such implementation of the program 100. Based on the results of the test, the program 100 may suggest new parameter values along with an explanation of why such values are chosen and the confidence of the suggested set of values 102. The devices 104 are reset with the parameter values with the highest confidence or best explanation. If a human tester (for example, an audiologist fine tuning a digital hearing aid or cochlear implant (CI)) is conducting the test using the computer program 100, he might decide to disregard the suggested set of values and set his own values if he finds the suggested parameter values and the explanation not particularly useful. Such a decision on the part of the tester is based generally on the tester's expert domain knowledge. In such a situation, the knowledge base 106 of the program 100 is updated with the knowledge of the expert used in determining an alternative set of values. At each iteration of the program 100, the agent 108 is tested with a new set of parameter values and, after testing, the program 100 suggests a new set of parameters. This procedure continues until a certain set of parameter values is obtained that helps the agent 108 perceive satisfactorily. Particularly advanced programs, utilizing a number of algorithms, may be able to suggest the optimum set of parameter values within a very short period of testing.

The purpose of testing is to determine the raw perceptual ability, independent of context and background knowledge, of the agent 108. A series of input signals is presented to the agent 108 whose environment is fitted with at least one perceptual device 104 set to certain parameter values. After each signal is presented, the agent 108 is given enough time to output a signal in response to its perceived signal, in accordance with instructions that the agent 108 has previously received. The output signal 110 corresponding to each input signal is recorded along with the time required for response. A metric captures the difference between the input signal and the agent's response in a meaningful way such that a model 112 of the agent's perceptual ability can be incrementally constructed using that metric and the device parameters.

At the end of each iteration, the test set creator or generator 114, utilizing one or more algorithms, modifies the parameters based on information received during the test. The next set of input signals are chosen on which the agent 108 should be tested, based on its strengths and weaknesses as evident from the model 112. A new test starts with the perceptual devices 104 set to new parameter values, again, based on the application of the algorithm to the information. An increase in response time indicates that either the agent 108 is having difficulty in perception or the agent 108 is getting fatigued. In the latter case, the agent 108, tester, or program 100 may opt to rest before further testing.

The model 112 describes the perceptual ability of the agent 108 with respect to the perceptual devices 104. Given an accurate model, one can predict the parameter values best suited for an agent 108. However, the model 112 is never complete until the agent 108 has been tested with all combinations of values for the parameters. Such testing is not feasible in a reasonable time for any complicated device. The model 112 is incremental and thus each prediction is based on the incomplete model derived prior to that iteration.

Figure 3:
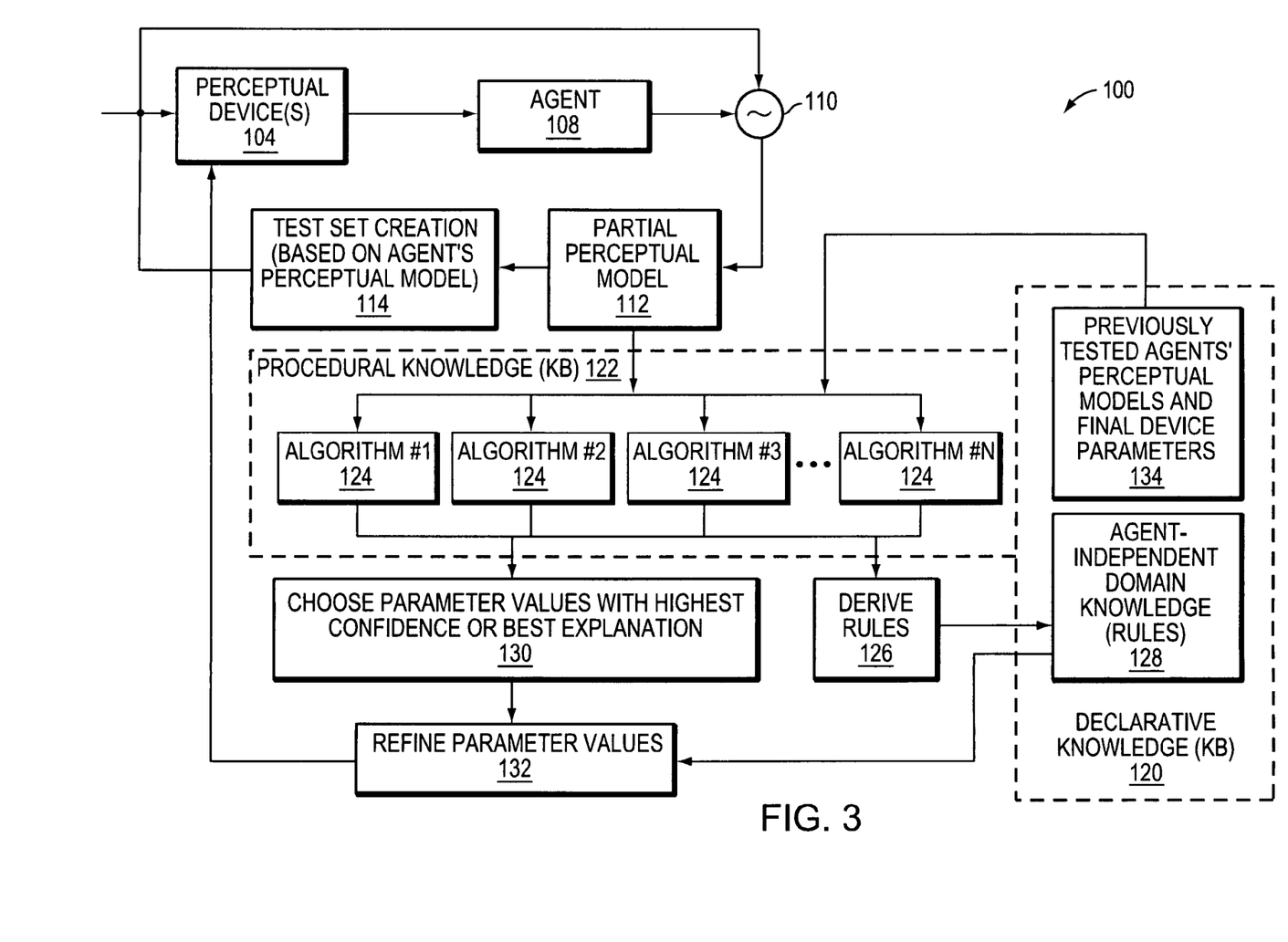
FIG. 3 is the schematic diagram of FIG. 2 incorporating a knowledge base in accordance with one embodiment of the present invention.

FIG. 3 presents another embodiment of the present invention incorporating a knowledge base into the computer program 100 of FIG. 2. The knowledge base (KB) of the computer program 100 stores knowledge in two forms—declarative 120 and procedural 122. Declarative knowledge 120 is stored as a set of statements useful for predicting a new set of parameter values 132 based on the model of the agent's perceptual ability. An example of declarative knowledge would include a situation where the agent 108 is a human with hearing loss, the device 104 is a CI, and his model 112 shows that he is weak in hearing the middle range of the frequency spectrum. In this case, the declarative knowledge 120 would include a statement that more CI channels should be associated with frequencies in that middle range than the higher or lower frequency ranges. Declarative knowledge can be readily applied, wherever appropriate, to make an inference. Often a user's previously tested parameters and device parameters 134 may be utilized with the declarative knowledge.

Procedural knowledge 122 is stored as procedures or algorithms that study the perceptual model 112 in order to make predictions for new parameter values. Each item of procedural knowledge is an independent algorithm 124 that studies the model 112 in a way which might involve certain assumptions about the model 112. These items of procedural knowledge may also utilize declarative knowledge 120 to study the model 112. Upon studying a model 112 and comparing it with the stored models of previously tested similar agents using similar devices, the algorithms may derive new rules 126 for storage as items of declarative knowledge 128. An example of procedural knowledge would include a situation where the agent is a human with hearing loss and the device is a CI. In this case, his model might be studied by an algorithm assuming that there exists a region in the model that represents the perceptual error minima of the agent. Hence, the algorithm will study the model hoping to find that minimum region and will predict appropriate parameter values for that minimum.

For any complicated perceptual device, the number of adjustable parameters can be large. The number of tests required to tune these parameters may even increase exponentially with the number of device parameters. One of the challenges faced by the proposed method is to reduce the number of tests so that the time required for tuning the parameter values can be reduced to a practical time period. One way to make the process more efficient is to utilize procedural knowledge 122. In the depicted embodiment, a number of procedures or algorithms 124 with very different assumptions are contemporaneously applied to the model 112. After application, each procedure provides its prediction of the parameters along with a confidence value for the prediction and an explanation of how the prediction was reached. These explanations are evaluated, either by a supervisory program or a tester, and that prediction that provides the best explanation is selected 130. By diversifying the assumptions used in studying the model 112, the chance of the method making inferior predictions may be significantly reduced. Since the different procedures essentially "compete" against each other, the resulting prediction is often better than the prediction reached by any single procedure operating alone. New items of procedural knowledge can be added to the system at will.

Figure 4:
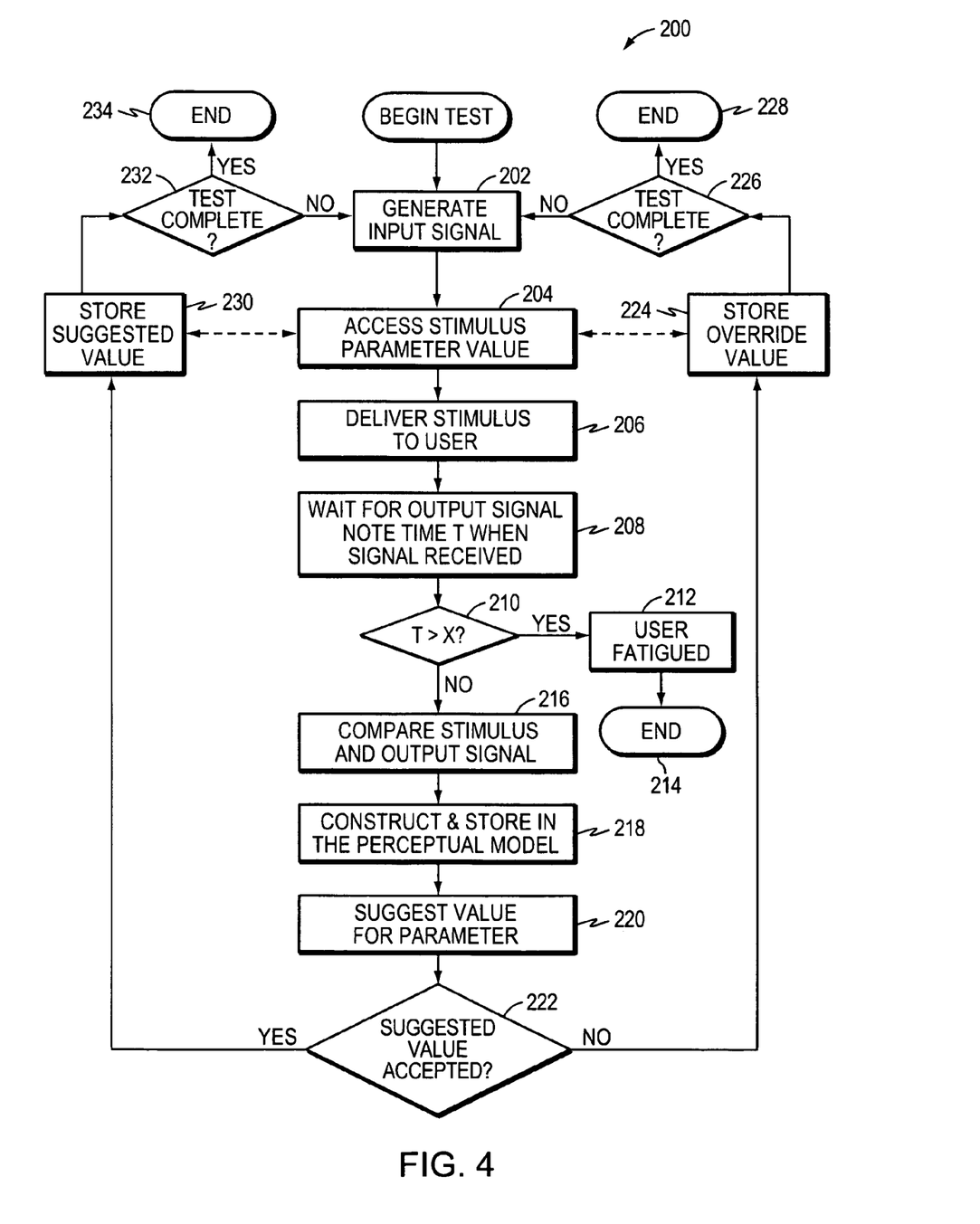
FIG. 4 is a flowchart of a testing procedure in accordance with one embodiment of the present invention.

FIG. 4 depicts an exemplary testing procedure 200 in accordance with one embodiment of the present invention. In this example, a user fitted with a CI is tested in the presence of an audiologist, who is monitoring the test. The program begins by generating an input signal 202. This input signal directs the CI to deliver a stimulus (e.g., a phoneme sound) to the user. Prior to sending the stimulus, however, the stimulus parameter value is accessed 204 by the program. This value may be either a factory default setting (usually when the device is first implanted), a previously stored suggested value, or a previously stored override value. The latter two values are described in more detail below.

A stimulus based on the parameter is then delivered to the user 206. The program waits for an output signal from the user 208. This received output signal may take any form that is usable by the program. For example, the user may repeat the sound into a microphone, spell the sound in a keyboard, or press a button or select an icon that corresponds to their perception of the sound. The program notes the time T when the output signal is received.

Upon receipt of the output signal from the user, the elapsed time is compared to a predetermined value 210. If the time exceeds this value, the program determines that the user is fatigued 212, and the program ends 214. If the elapsed time does not exceed the threshold, however, the output signal and stimulus are compared 216 to begin analysis of the results. The difference between the output signal from the user and the stimulus sent from the CI to the user are used to construct the perceptual model 218. Next, the program suggests a value for the next parameter to be tested 220.

At this point, the audiologist may optionally decide whether or not to utilize the suggested value 222 for the next test procedure, based on his or her knowledge base or other factors that may not be considered by the program. If the audiologist overrides the suggested value with a different value, this override value is stored 224 to be used for the next test. The program then determines if the test is complete 226, and may terminate the test 228 if required or desired by the user.

The test may be determined to be complete for a number of reasons. For example, the user or audiologist may be given the option at this point (or at any point during the test) to terminate testing. The program may determine that during one or more iterations of the test, the user's response time, as measured in step 210, increased such that fatigue may be a factor, warranting termination of the testing. Additionally, the program may determine that, based on information regarding the tested device or the program itself, all iterations or options have been tested. In such a case, the program may determine that no further parameter adjustment would materially improve the operation of the device or the program. Also, the program may interpret inconsistent information at this point as indicative of an error condition that requires termination. Other procedures for terminating testing are known to the art.

Returning to step 222, if the suggested value is accepted, this value is then stored for later use in a subsequent test 230. In an alternative embodiment of the program, the program may be operated without the assistance of an audiologist. In this case, acceptance of the suggested value would be the default response to the suggested value. In this way, the test may be utilized without the involvement of an audiologist. Thus, the program, with few modifications, could allow the user to self-tune his device remotely, potentially over an internet connection or with a stand-alone tuning device. After the suggested value is stored, a determination to continue the test 232 (having similar considerations as described in step 226), may be made prior to ending the test 234.

The optimization methods of the current invention may be utilized with virtually any metric that may be used to test people that utilize digital hearing devices. One such metric is disclosed in, for example, U.S. Pat. No. 7,206,416 to Krause et al., the entire disclosure of which is hereby incorporated by reference herein in its entirety, and will be discussed herein as one exemplary application of the optimization methods.

Figure 5:
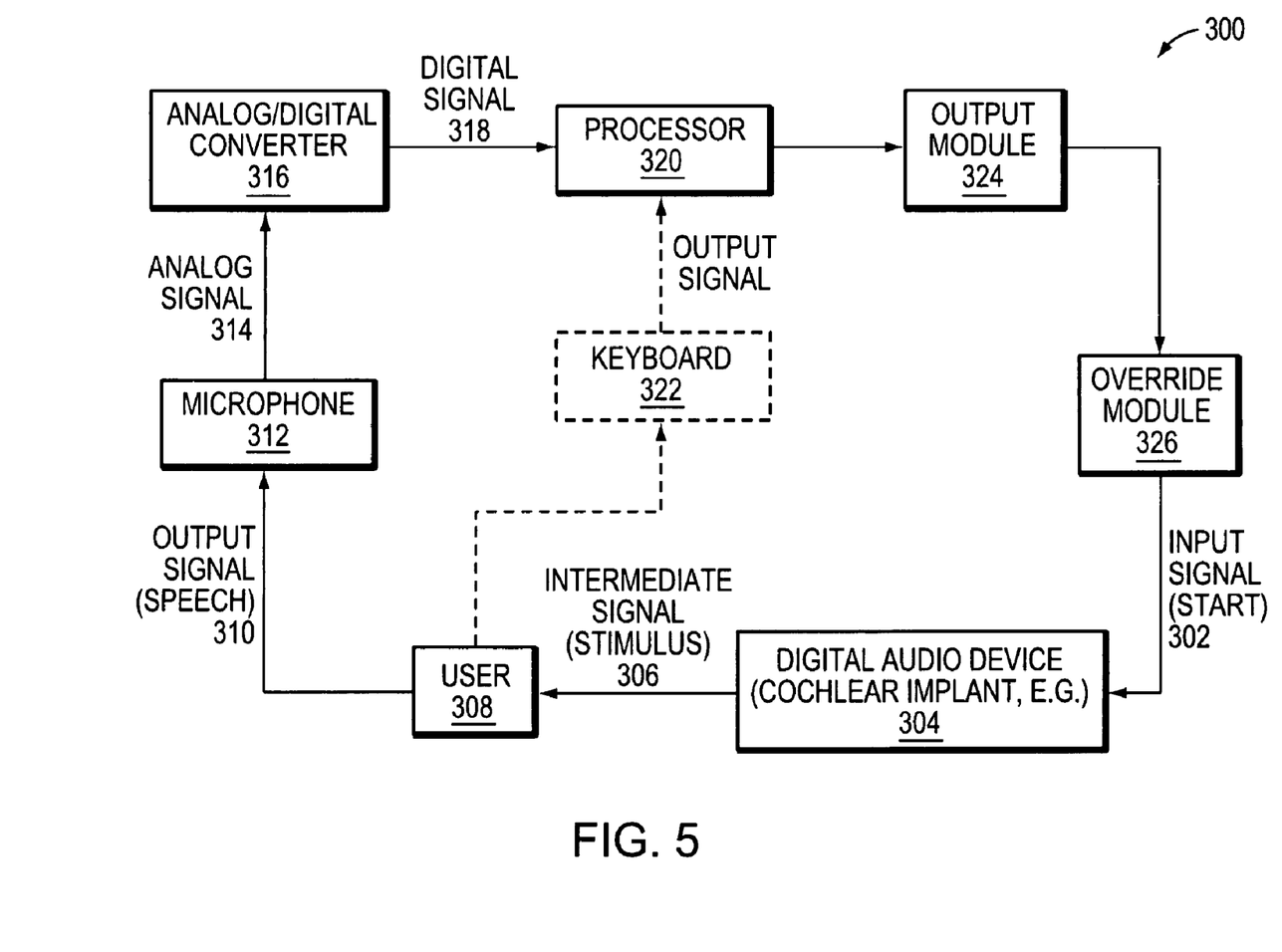
FIG. 5 is a schematic diagram of a testing system in accordance with one embodiment of the present invention.

A typical testing system 300 is depicted in FIG. 5. The testing procedure tests the raw hearing ability, independent of context and background knowledge, of a hearing-impaired person. As the procedure begins, an input signal 302 is generated and sent to a digital audio device, which, in this example, is a CI 304. Based on the input signal, the CI will deliver an intermediate signal or stimulus 306, associated with one or more parameters, to a user 308. At the beginning of a test procedure, the parameters may be factory-default settings. At later points during a test, the parameters may be otherwise defined, as described below. In either case, the test procedure utilizes the stored parameter values to define the stimulus (i.e., the sound).

After a signal is presented, the user is given enough time to make a sound signal representing what he heard. The output signal corresponding to each input signal is recorded along with the response time. If the response time exceeds a predetermined setting, the system determines that the person may be getting fatigued and will stop the test. The output signal 310 may be a sound repeated by the user 308 into a microphone 312. The resulting analog signal 314 is converted by an analog/digital converter 316 into a digital signal 318 delivered to the processor 320. Alternatively, the user 308 may type a textual representation of the sound heard into a keyboard 322. In the processor 320, the output signal 310 is stored and compared to the immediately preceding stimulus.

Based on the user response, an algorithm decides the user's strengths and weaknesses and stores this information in an internal perceptual model. Additionally, the algorithm suggests a value for the next test parameter, effectively choosing the next input sound signal to be presented. This new value is delivered via the output module 324. If an audiologist is administering the test, the audiologist may choose to ignore the suggested value, in favor of their own suggested value. In such a case, the tester's value would be entered into the override module 326. Whether the suggested value or the tester's override value is utilized, this value is stored in a memory for later use (likely in the next test). These tests may be repeated with different sounds until the CI performance is optimized or otherwise modified, the user fatigues, etc. In one embodiment, the test terminates when the user's strengths and weaknesses with respect to the current CI device parameters are comprehensively determined. A new test starts with the CI device set to new parameter values.

The disclosed system utilizes any number of algorithms that may operate substantially or completely in parallel to suggest parameter values in real time. Exemplary algorithms include (1) computing a reduced set of phonemes (input sound signals) for testing a person based on his strengths and weaknesses from past tests and using the features of the phonemes, thereby reducing testing time considerably; (2) computing a measure of performance for a person from his tests involving features of phonemes and their weights; (3) classifying a person based on their strengths and weaknesses as obtained from previous tests; and (4) predicting the parameter setting of a CI device to achieve optimum hearing for a person using his perceptual model and similar people's optimal device settings. These algorithms will be explained in more detail below. In addition to these algorithms, other embodiments utilize alternative methodologies to compute parameter values. For example, predetermined parameter values may be selected from a lookup table containing parameter value combinations based on a person's known or predicted strengths and weaknesses based on results from tests.

In human language, a phoneme is the smallest unit of distinguishable speech. Phonemes may be utilized in testing. For example, the input signal may be chosen from a set of phonemes from the Iowa Medial Consonant Recognition Test. Both consonant phonemes and vowel phonemes may be used during testing, though vowel phonemes may have certain disadvantages in testing: they are too easy to perceive and typically do not reveal much about the nature of hearing loss. It is known that each phoneme is characterized by the presence, absence or irrelevance of a set of nine features—Vocalic, Consonantal, Compact, Grave, Flat, Nasal, Tense, Continuant, and Strident. These features are arranged hierarchically such that errors in recognizing a feature "higher" up in the hierarchy would result in more speech recognition problems because it would affect a greater number of phonemes.

A person's performance in a test can be measured by the number of input sound signals (i.e., phonemes, although actual words in any language may also be used) he fails to perceive. This type of basic testing, however, may fail to capture the person's strengths and weaknesses because many phonemes share similar features. For example, the phonemes '\f' and '\p' differ only in one out of the nine features called Continuant. A person who fails to perceive '\p' due to an error in any feature other than Continuant will also fail to perceive '\f' and vice versa. Thus, counting the number of phoneme errors would obtain less accurate results because feature errors are giving rise to phoneme errors. Due to the same reason, in order to reduce the phoneme errors, it may be desirable to focus testing on the feature errors.

In the present invention, a person's performance in a test is measured by the weighted mean of the feature errors, given by:

$$\xi = \frac{\sum_{i=1}^{9} w_i n_i}{\sum_{i=1}^{9} w_i} \tag{i}$$

where $w_i$ is the weight and $n_i$ is the number of errors in the ith feature of the hierarchy. The weights of the features are experimentally ascertained to be {0.151785714, 0.151785714, 0.142857143, 0.098214286, 0, 0.142857143, 0.125, 0.125, 0.0625}. Other weights may be utilized as the testing procedures evolve for a given user or group of users. The actual weight utilized in experimentation to optimize may include other values and potentially may be dependent upon testing, the language being used, and other variables. Acceptable results may be obtained utilizing other weightings.

This manner of testing provides a weighted error representing the user's performance with a set of parameter values. If a person is tested with all possible combinations of parameter values, the result can be represented as a weighted error surface in a high-dimensional space, where the dimension is one more than the number of parameters being considered. In this error surface, there exists a global minimum and one or more local minima. In general, while the person's performance is good at each of these local minima, his performance is the best at the global minimum. One task of the computer program is to predict the location of the global minimum or at least a good local minimum within a short period of testing.

The perceptual model may be represented in a number of ways, such as using a surface model, a set of rules, a set of mathematical/logical equations and inequalities, and so on, to obtain results. In the case of the surface model, due to the presence of many parameters, a very high-dimensional error surface may be formed. The minimum amount of data required to model such a surface increases exponentially with the number of dimensions leading to the so-called "curse of dimensionality." There is therefore an advantage to reducing the number of parameters. In one embodiment, the large number of parameters are reduced to three-"stimulation rate," "Q-value," and "map number." The stimulation rate and Q-value can dramatically change a person's hearing ability. The map number is an integer that labels the map and includes virtually all device parameters along with a frequency allocation table. Changing any parameter value or frequency allocation to the different channels would constitute a new map with a new map number. Thus, the error surface is reduced to a four-dimensional space, thereby considerably reducing the minimum amount of data required to model the surface. Each set of three parameter values constitutes a point. Only points at which a person has been tested, called sampled points, have a corresponding weighted error. The error surface is constituted of sampled points.

Adjusting parameters to reduce errors in one feature may lead to an increase in error in another feature. In order to adjust parameters such that the overall performance is enhanced, one should strive to reduce the total weighted error as described by equation (i). Described below are a number of algorithms for predicting parameters from a person's past performance, represented by the error surface, and values for the device parameters that have the maximum potential for helping him achieve optimum hearing.

Figure 6:
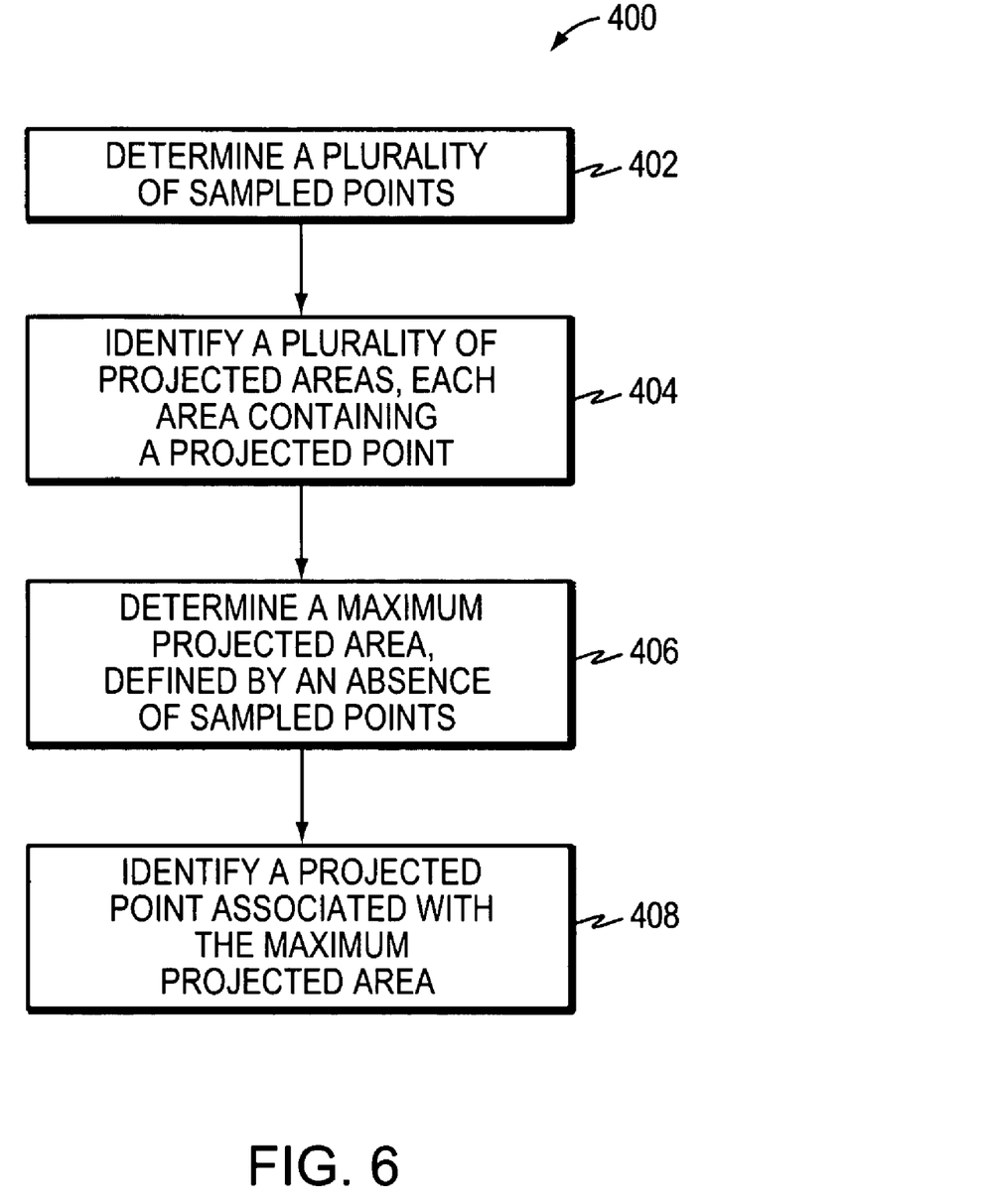
FIG. 6 is a flowchart of a uniform sampling algorithm in accordance with one embodiment of the present invention.

FIG. 6 depicts a flowchart for an exemplary uniform sampling algorithm 400. First, the algorithm 400 determines a plurality of sampled points 402, the remaining points are the projected or unsampled points. The algorithm then identifies a number of projected areas, each projected area containing no sampled points 404. In general, the projected areas may be various geometric shapes and may be centered on the projected points. Other locations of the areas relative to the projected points are also contemplated. For example, the projected points may be located a set distance from the edge of the projected areas, or may occupy a defined location along the outer limits of the projected areas (e.g., at an angle of the area boundary formed by the intersection of two lines). Moreover, the projected areas may be any shape, although circular shapes are generally desirable, due in part to the simplicity in computation. Areas having oval, square, triangular, or undefined shapes, for example, are also contemplated.

Next, a first projected area is determined by the algorithm; the first projected area is characterized by an absence of any of the plurality of sampled points 406. A projected point may then be associated with this first projected area (e.g., the center point of the area may be identified), so as to uniformly reduce the size of the unsampled area for subsequent iterations 408. In certain embodiments, the first projected area may be a maximum area, based on the size of the first projected area relative to the sizes of the other of the plurality of projected areas. In other embodiments, the first projected area may be one of the projected areas having a size substantially similar to the average size of a number of the plurality of projected areas.

In a particular embodiment of a uniform sampling algorithm, the algorithm uniformly samples the space irrespective of the nature of a person's performance in tests. The assumption is that the error surface is perfectly random and that all locations are equally likely to be the optimum. When two or more locations are equally likely, the one that is in the most secluded area is chosen. Let S be the set of all points, $S_{sampled}$ be the set of sampled points, and $S_{unsampled}$ be the set of unsampled points ($S=S_{sampled} \cup S_{unsampled}$). A point $p \in S_{unsampled}$ is considered to be more plausible than any point $q \in S_{unsampled}$ if and only if p has the largest neighborhood. The neighborhood of a point u is measured by the minimum distance it has to any of the sampled points. Mathematically, this is written as:

$$\forall q \in S_{unsampled}, \text{Plausibility}(p) \geq \text{Plausibility}(q) \Leftrightarrow p \in \quad \text{(ii)}$$

$$S_{unsampled} \wedge \text{Neighborhood}(p) \geq$$

$$\text{Neighborhood}(q) \quad \text{Neighborhood}(u) = \min_{v \in S_{sampled}}(\text{Distance}(u, v))$$

The confidence in the chosen point p is given by $$\text{Confidence}(p) = \frac{100\%}{\#(S_{unsampled})} \quad \text{(iii)}$$

where #(S) denotes the cardinality of the set S.

This strategy limits the over-sampling of one region and the under-sampling of another. The uniform sampling algorithm has two major advantages—it helps to start the process of prediction for any person without any prior knowledge, and it produces a valid prediction irrespective of the number and nature of sampled points. Thus, even though the algorithm is very simple and based on simple assumptions, it is particularly effective, even in situations where other more sophisticated algorithms fail.

Figure 7:
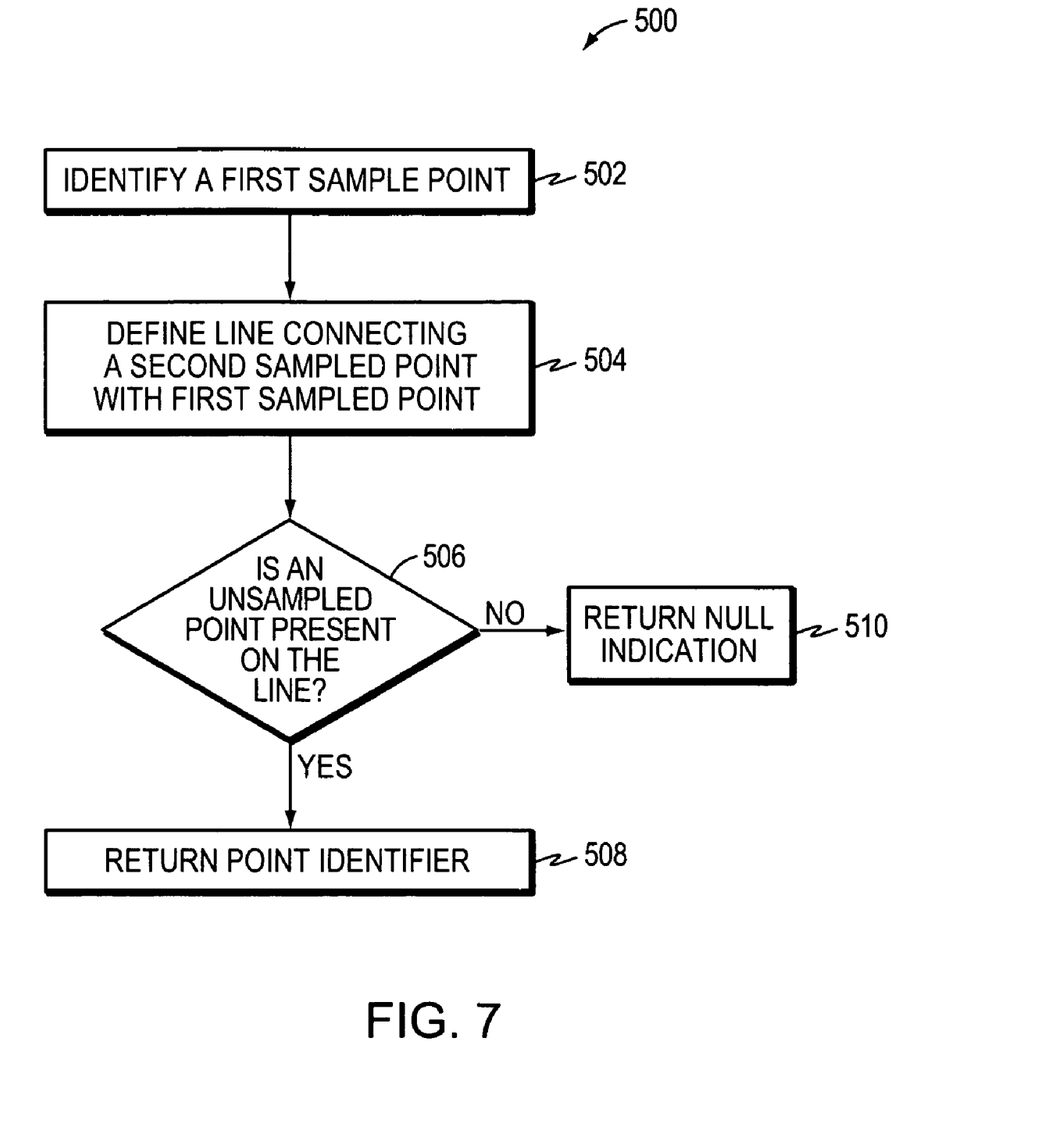
FIG. 7 is a flowchart of a neighborhood sampling algorithm in accordance with one embodiment of the present invention.

FIG. 7 depicts a flowchart for an exemplary neighborhood sampling algorithm 500. In this algorithm, a first sampled point is identified 502. Another sampled point is then located on a line connecting the two sampled points 504. This line may be selected based on its slope. In one embodiment, the slope of the line is the maximum downward slope from a second sampled point to the first sampled point, wherein the maximum downward slope is based on a comparison of the slope of all lines to the first sampled point from any number of other sampled points. This may be quickly measured by comparing the slopes of the two steepest lines in a set to determine the maximum slope. The two lines, then, would share the first sample point where the lines intersect; one line would then be defined by the second sampled point, and the other would be defined by a third sampled point, for example. The algorithm 500 next determines if an unsampled or projected point is present on the line proximate the first sample point 506. If so, that new unsampled or projected point is identified 508. If no such projected point is present, a null set is returned 510.

In a particular embodiment, the neighborhood sampling algorithm computes a highly plausible point based on the merits of the sampled points. The assumption is that any of the minima is not constituted of a single point but by a small coherent region consisting of a few points, since a single-point minimum can as well be an experimental error. Since any minimum, local or global, is a region, it is highly plausible that a point in the immediate neighborhood of a sampled point with low weighted error will also have low weighted error. In fact, the weighted error at that point might be even lower than the sampled point if it lies on the downward slope from the sampled point.

The slope from a sampled point a to a sampled point b is defined as $$\text{Slope}(a, b) = \frac{(\xi(b) - \xi(a))^3}{|L_{SR}(b) - L_{SR}(a)| \times |L_Q(b) - L_Q(a)| \times |L_M(b) - L_M(a)|} \quad \text{(iv)}$$

where $\xi(p)$ denotes the weighted error at point p (see equ. (i)), $L_{SR}(p)$, $L_Q(p)$, and $L_M(p)$ denote the locations corresponding to stimulation rate, Q-value, and map number at a point p respectively. For example, if the stimulation rates possible are 250 Hz, 500 Hz, 720 Hz, 900 Hz, 1200 Hz, 1800 Hz, and 2400 Hz, then location of 250 Hz is 1, 500 Hz is 2, 900 Hz is 4, etc. This is similar for Q-values and map numbers. The locations of the parameter values instead of the values themselves are considered because experiments show that the nature of the error surface does not necessarily vary depending on the values. For example, experiments show that the change in error surface between stimulation rates of 1800 Hz and 2400 Hz is not necessarily twice that between 900 Hz and 1200 Hz even though the difference in the parameter values are twice as much.

At any instant, this algorithm computes the best sampled point with unsampled or projected points in its immediate neighborhood. A point in its immediate neighborhood is investigated if the best sampled point is good enough. A sampled point is considered good enough if its "goodness" is less than a predetermined threshold. The goodness of a sampled point p is given by $$Goodness(p) = 1 - \frac{\xi(p)}{\xi(\text{default point})} \quad (v)$$

The algorithm may begin processing by first determining the goodness of a number of previously sampled points. That goodness may be a confidence assigned to each sampled point that helps the algorithm to determine a starting sampled point upon which to begin testing. If no point is good enough, the algorithm will not investigate the neighborhood of any point. If a number of sampled points are good enough, the best point is chosen. A point in its immediate neighborhood is chosen for investigation such that the point lies on the maximum downward slope from one of the other sampled points to the best sampled point. Thus, the chosen neighborhood point q satisfies the following constraints:

$$\text{Goodness } (p_{best}) \geq \text{threshold Slope } (u, p_{best}) = \quad (vi)$$
$$\max_{v \in S_{sampled}, v \neq p_{best}} (\text{Slope}(v, p_{best}))$$
$$\text{On } (q, \overrightarrow{up_{best}}) = \text{True}$$
$$|L_{SR}(q) - L_{SR}(p_{best})| = 1$$
$$|L_Q(q) - L_Q(p_{best})| = 1$$
$$|L_M(q) - L_M(p_{best})| = 1$$
$$q \in S_{unsampled}$$

where $p_{best}$ the best sampled point. The confidence in the chosen point q is given by $$Confidence(q) = \frac{100\%}{\#(\{u : u \in S_{unsampled} \land |L_{SR}(u) - L_{SR}(p_{best})| = 1 \land |L_Q(u) - L_Q(p_{best})| = 1 \land |L_M(u) - L_M(p_{best})| = 1\})} \quad (vii)$$

Unlike the uniform sampling algorithm, the neighborhood sampling algorithm cannot predict without prior knowledge since it requires at least two points to start the process. Nevertheless it is a very strong algorithm that investigates in a greedy manner the neighborhood of points where the person has done very well. Given the assumption that the minima in the error surface is a region as opposed to a point, the neighborhood sampling algorithm can discover that region faster than most other algorithms.

Figure 8:
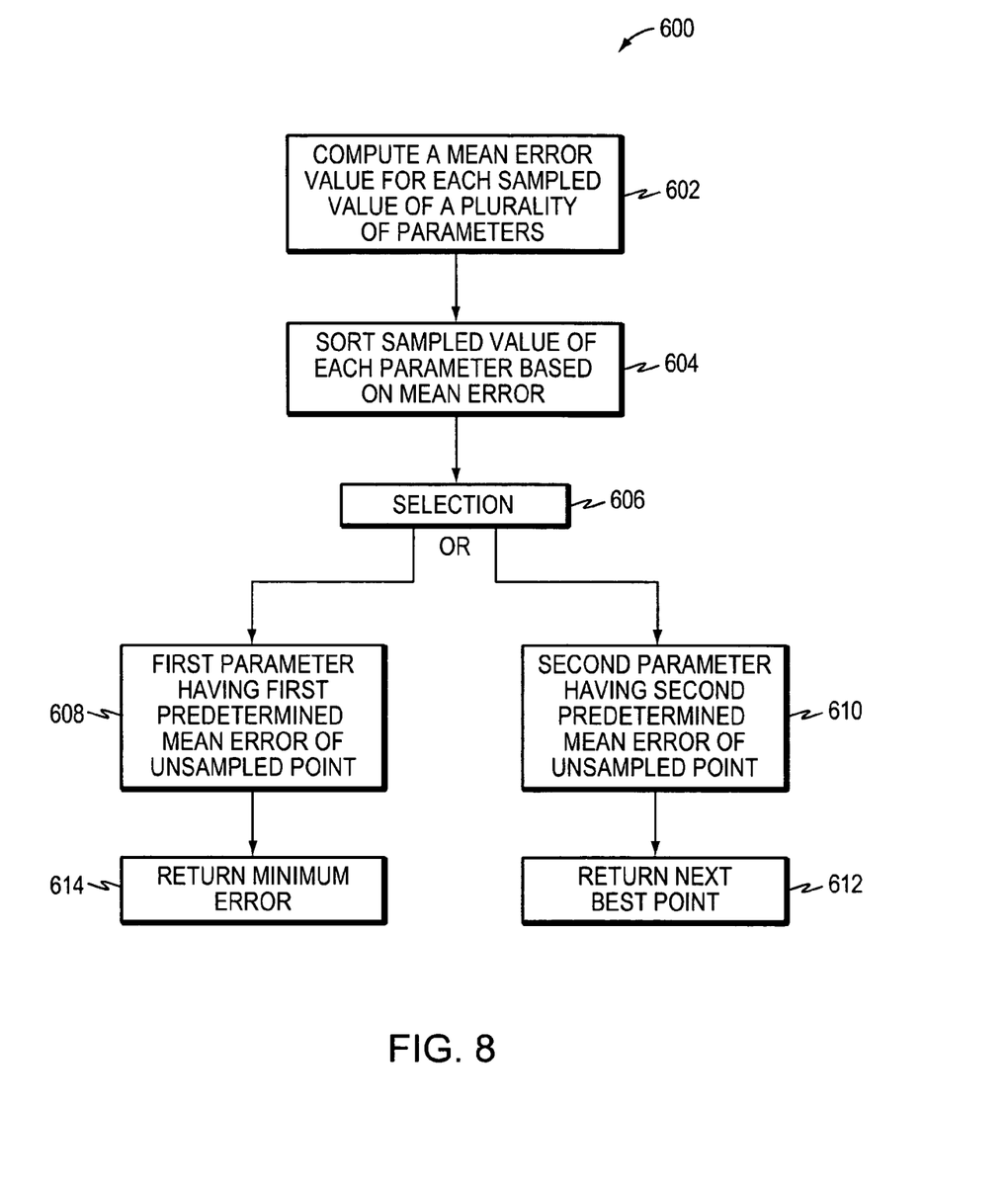
FIG. 8 is a flowchart of an average sampling algorithm in accordance with one embodiment of the present invention.

FIG. 8 depicts a flowchart for the average sampling algorithm 600. In this algorithm, a mean error of each sampled value of a plurality of parameters is first computed 602. The sampled value of each of the plurality of parameters are then sorted based on the mean error 604. In some embodiments, this sorting may take place in ascending order; in other embodiments sorting may take place in descending order. Next, one of a plurality of parameters is selected by the algorithm 606. In one embodiment, the selection is made between a first parameter having a first predetermined mean error of an unsampled or projected point 608 and a second parameter having a second predetermined mean error of an unsampled point 610. This second predetermined error may be characterized as a next best point 612. In certain embodiments, the first predetermined mean error is a minimum error 614.

In one embodiment, the average sampling algorithm computes a highly plausible point based on the merit of the already sampled parameter values. The assumption is that the best point lies on the parameter value that has the best average performance. Thus, if a person's performance at a stimulation rate of 900 Hz is better than the other stimulation rates, then it is highly probable that the person's best performance will be at a stimulation rate of 900 Hz. Hence, the best point lies at the intersection of the best average parameter values.

The average performance of a person at a parameter value u, where the parameter constitutes the first coordinate of a point, is given by $$\overline{Performance}(u) = \frac{\sum_{p \in S_{sampled} \land p(1) = u} \xi(p)}{\#(\{p : p \in S_{sampled} \land p(1) = u\})} \quad (viii)$$

p(1) denotes the value at the first coordinate of the sampled point p. Similarly, the average performance of a person at a parameter value v, where the parameter constitutes the second coordinate of a point, is given by $$\overline{Performance}(v) = \frac{\sum_{p \in S_{sampled} \land p(2) = v} \xi(p)}{\#(\{p : p \in S_{sampled} \land p(2) = v\})} \quad (ix)$$

p(2) denotes the value at the second coordinate of the sampled point p, and so on.

Let $\Phi(i)$ be the set of all values for the ith parameter, $\Phi_{sampled}(i)$ be the set of sampled values for the ith parameter, and $\Phi_{unsampled}(i)$ be the set of unsampled values for the ith parameter ($\Phi = \Phi_{sampled} \cup \Phi_{unsampled}$). At any instant, the average sampling algorithm computes the most plausible point q such that q satisfies the following constraints:

$$Performance(q(1)) = \min_{p(1) \in \Phi_{sampled}(1)} (Performance(p(1))) \quad (x)$$
$$Performance(q(2)) = \min_{p(2) \in \Phi_{sampled}(2)} (Performance(p(2)))$$
$$Performance(q(3)) = \min_{p(3) \in \Phi_{sampled}(3)} (Performance(p(3)))$$
$$q \in S_{unsampled}$$

The confidence in the chosen point q is given by $$Confidence(q) = \frac{100\%}{\#(\{p : p \in S_{unsampled} \land p(1) \in \Phi_{sampled}(1) \land p(2) \in \Phi_{sampled}(2) \land p(3) \in \Phi_{sampled}(3)\})} \quad (xi)$$

Clearly, a substantial number of points should be sampled before the average performances of the different parameters can be compared. Even after that, the most probable point computed by the algorithm might not belong to the set of unsampled points. When such a case happens, the algorithm returns the next best point. This algorithm is a powerful tool for computing globally a very good potential point. While the neighborhood sampling algorithm looks for a point from a small region, the average sampling algorithm considers all sampled parameter values to compute a point. Thus, they are very different and powerful algorithms.

The three algorithms described above have their own characteristics, and have certain advantages and disadvantages in application. While each algorithm may perform optimization acceptably on its own, the operation of two or more of the algorithms in parallel should increase the efficiency of the process. In further embodiments of the invention, additional or other algorithms may also be utilized.

While there have been described herein what are to be considered exemplary and preferred embodiments of the present invention, other modifications of the invention will become apparent to those skilled in the art from the teachings herein. The particular methods of manufacture and geometries disclosed herein are exemplary in nature and are not to be considered limiting. It is therefore desired to be secured in the appended claims all such modifications as fall within the spirit and scope of the invention. Accordingly, what is desired to be secured by Letters Patent is the invention as defined and differentiated in the following claims.

What is claimed is:

1. A system for modifying a controllable stimulus generated by a digital audio device in communication with a human user, the system comprising:
    a test set generator for generating a test set for the digital audio device, the digital audio device sending a stimulus to the human user, the stimulus defined at least in part by a parameter, the parameter comprising a value;
    a signal receiver for receiving an output signal from the human user, the output signal based at least in part on a perception of the stimulus by the human user;
    a perceptual model module receiving and storing information concerning the output signal from the signal receiver; and
    a parameter value generator for applying at least one algorithm to the information and modifying a parameter value based at least in part on the application of the algorithm to the information, wherein the at least one algorithm comprises a uniform sampling algorithm, and wherein the parameter value generator further comprises:
        a point identification module for identifying a plurality of sampled points;
        an area identification module for identifying a plurality of projected areas,
    wherein each projected area is characterized by an absence of any of the plurality of sampled points; and
        a projected point identification module for identifying a projected point associated with a first projected area so as to reduce the size of an unsampled area for subsequent iterations.

2. The system of claim 1, wherein the perceptual model comprises a surface model.

3. The system of claim 1, wherein a first projected area comprises an area greater than an area of each of the plurality of projected areas.

4. The system of claim 1, wherein the projected areas are circles.

5. The system of claim 4, wherein the projected points are the centers of the circles.

6. A system for modifying a controllable stimulus generated by a digital audio device in communication with a human user, the system comprising:
    a test set generator for generating a test set for the digital audio device, the digital audio device sending a stimulus to the human user, the stimulus defined at least in part by a parameter, the parameter comprising a value;
    a signal receiver for receiving an output signal from the human user, the output signal based at least in part on a perception of the stimulus by the human user;
    a perceptual model module receiving and storing information concerning the output signal from the signal receiver;
    a parameter value generator for applying at least one algorithm to the information and modifying a parameter value based at least in part on the application of the algorithm to the information, wherein the at least one algorithm comprises an average sampling algorithm, and wherein parameter value generator further comprises:
        a mean error calculator for computing a mean error of each of a sampled value of a plurality of parameters;
        a sorter for sorting the sampled value of each of the plurality of parameters based at least in part on the mean error; and
        a point selector for selecting at least one of (i) a projected point comprising a first predetermined mean error of a parameter and (ii) a projected point comprising a second predetermined mean error.

7. The system of claim 6, wherein the perceptual model comprises a surface model.

8. The system of claim 6, wherein the sorter sorts the sampled values in ascending order.

9. The system of claim 6, wherein the first predetermined mean error is a minimum error.

10. The system of claim 6, wherein the second predetermined error comprises a next best point.

* * * * *